(12) United States Patent
Na et al.

(10) Patent No.: US 11,724,043 B2
(45) Date of Patent: Aug. 15, 2023

(54) APPARATUS AND METHOD FOR INTRACRANIAL DRUG INJECTION

(71) Applicant: Samsung Life Public Welfare Foundation, Seoul (KR)

(72) Inventors: Duk Lyul Na, Seoul (KR); Jeongmin Lee, Seoul (KR); Wooram Jung, Seoul (KR); Jung-Il Lee, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 342 days.

(21) Appl. No.: 16/760,351

(22) PCT Filed: Oct. 31, 2018

(86) PCT No.: PCT/KR2018/013097
§ 371 (c)(1),
(2) Date: Apr. 29, 2020

(87) PCT Pub. No.: WO2019/088690
PCT Pub. Date: May 9, 2019

(65) Prior Publication Data
US 2021/0369979 A1    Dec. 2, 2021

(30) Foreign Application Priority Data

Nov. 1, 2017 (KR) .......................... 10-2017-0144757

(51) Int. Cl.
*A61M 5/32*    (2006.01)

(52) U.S. Cl.
CPC ............ *A61M 5/3287* (2013.01); *A61M 5/32* (2013.01); *A61M 2210/0693* (2013.01)

(58) Field of Classification Search
CPC ...... A61M 5/3287; A61M 5/32; A61M 5/329; A61M 5/3293; A61M 2210/0693
See application file for complete search history.

(56) References Cited

U.S. PATENT DOCUMENTS 3,417,745 A * 12/1968 Emanuel ................ A61B 1/002
600/116
4,629,451 A * 12/1986 Winters ............ A61M 39/0247
606/169

(Continued)

FOREIGN PATENT DOCUMENTS

CN    1516607 A    7/2004
CN    101896220 A    11/2010

(Continued)

OTHER PUBLICATIONS

International Search Report (including English translation of ISR) and Written Opinion prepared by Korean Intellectual Property Office, acting as the International Searching Authority, for international application PCT/KR2018/013097 dated Mar. 19, 2019.

*Primary Examiner* — Nathan R Price
*Assistant Examiner* — Mark A Igel
(74) *Attorney, Agent, or Firm* — McCarter & English, LLP

(57) ABSTRACT

The present disclosure provides an apparatus for intracranial drug injection including a body unit having a through-hole extending between a first opening in a topmost surface and a second opening in a bottommost surface, a cap unit having a shape corresponding to at least a part of an inner surface of the through-hole and being inserted into the first opening to cover the first opening, and a tube unit having one end coupled to the second opening and another end extending toward an affected brain lesion.

18 Claims, 11 Drawing Sheets

(56) References Cited

U.S. PATENT DOCUMENTS

| | | | | |
|---|---|---|---|---|
| 4,903,707 | A | * | 2/1990 | Knute ............... A61B 17/3403 600/561 |
| 5,554,148 | A | * | 9/1996 | Aebischer ........... A61M 31/002 604/265 |
| 5,695,490 | A | * | 12/1997 | Flaherty ............ A61M 39/0208 604/288.02 |
| 5,865,842 | A | * | 2/1999 | Knuth ................ A61B 5/6864 607/116 |
| 5,954,687 | A | * | 9/1999 | Baudino .............. A61M 25/02 604/93.01 |
| 6,852,106 | B2 | | 2/2005 | Watson et al. |
| 10,099,046 | B2 | | 10/2018 | Lee et al. |
| 2001/0003156 | A1 | * | 6/2001 | Gill ................. A61B 90/11 606/130 |
| 2002/0138068 | A1 | * | 9/2002 | Watson ............. A61M 39/0208 604/288.03 |
| 2004/0215162 | A1 | * | 10/2004 | Putz ................ A61B 5/031 607/116 |
| 2005/0027234 | A1 | * | 2/2005 | Waggoner .......... A61B 10/0045 604/8 |
| 2009/0306501 | A1 | * | 12/2009 | Flint ................ A61B 8/12 600/437 |
| 2012/0083742 | A1 | * | 4/2012 | Nelson ................ A61B 90/11 604/175 |
| 2015/0011938 | A1 | * | 1/2015 | Gill ................. A61B 90/11 606/108 |
| 2016/0235960 | A1 | * | 8/2016 | Lee ................. A61M 39/0247 |
| 2017/0119432 | A1 | * | 5/2017 | McKay ............. A61B 18/0218 |
| 2017/0135778 | A1 | * | 5/2017 | Gill ................. A61M 25/0026 |
| 2018/0015273 | A1 | * | 1/2018 | Gill ................. A61P 25/28 |
| 2018/0140810 | A1 | * | 5/2018 | Cataltepe ............ A61M 25/007 |
| 2019/0167964 | A1 | * | 6/2019 | Lewis ................ A61M 39/04 |

FOREIGN PATENT DOCUMENTS

| | | |
|---|---|---|
| CN | 105611956 A | 5/2016 |
| DE | 696 32 819 T2 | 7/2005 |
| JP | 2010-540200 A | 12/2010 |
| KR | 10-2011-0000795 A | 1/2011 |
| KR | 20140137308 A * | 5/2014 |
| KR | 10-1405610 B1 | 6/2014 |
| KR | 10-2014-0137308 A | 12/2014 |
| KR | 20140137308 A * | 12/2014 |
| WO | WO 2009/047490 A2 | 4/2009 |
| WO | WO 2013/117661 A2 | 8/2013 |
| WO | WO 2014/189253 A2 | 11/2014 |

* cited by examiner

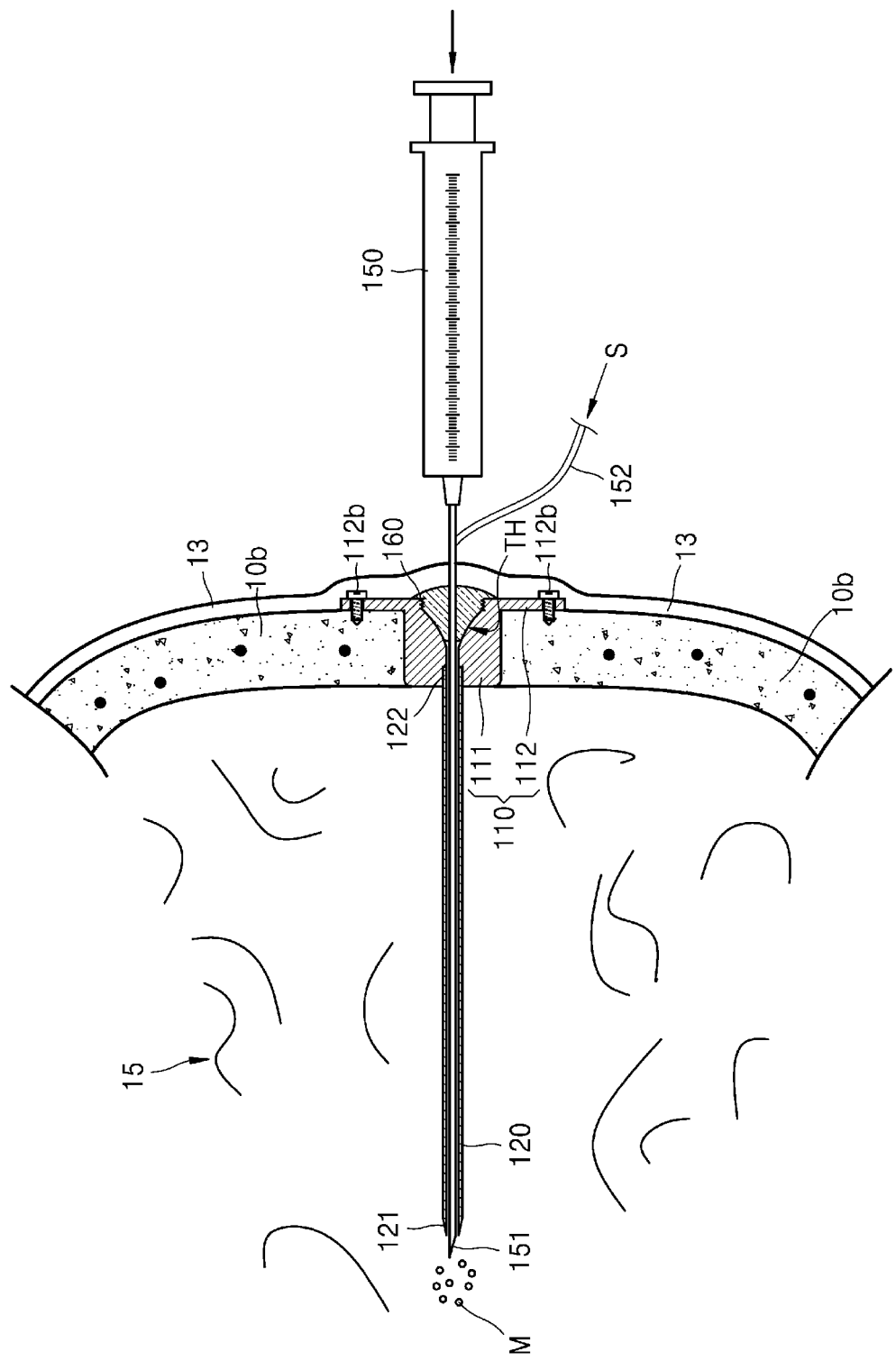

APPARATUS AND METHOD FOR INTRACRANIAL DRUG INJECTION

CROSS-REFERENCE TO RELATED APPLICATIONS

This application is the National Stage entry under 35 U.S.C. § 371 of International Application Number PCT/KR2018/013097 filed on Oct. 31, 2018, published on May 9, 2019 under publication number WO 2019/088690 A1, which claims the benefit of priority under 35 U.S.C. § 119 of Korean patent application number 10-2017-0144757 filed Nov. 1, 2017.

TECHNICAL FIELD

Embodiments of the present disclosure relate to an apparatus for intracranial drug injection and a method for intracranial drug injection, and more specifically, to an apparatus for intracranial drug injection and a method for intracranial drug injection, by which stem cells or brain disease treatment drugs may be easily and repeatedly administered into an affected brain lesion of a patient suffering from a degenerative brain disease such as Alzheimer's dementia.

BACKGROUND ART

Alzheimer's dementia is one of major causes of dementia in the elderly, and histopathologically exhibits characteristics such as overall atrophy of the brain, expansion of ventricles, Neurofibrillary tangles, and neuritic plaques.

Currently, it is known that approximately 3% of the population aged 65 to 74, approximately 19% of the population aged 75 to 84, and 50% of the population aged 85 or older suffer from this disease in the United States, and according to a recent study on rural areas in Korea, it is also reported that approximately 21% of the rural population aged 60 or older suffers from dementia and 63% of the rural population suffers from Alzheimer's dementia. With a rapid increase in the elderly population due to an aging society, the number of patients suffering from Alzheimer's dementia is expected to increase further.

A method of directly injecting stem cells into the brain of a patient has been studied as a method for treatment of patients suffering from Alzheimer's dementia which is becoming serious. Although various methods have been attempted to deliver therapeutic agents for Alzheimer's disease into the brain, in the case of administration through blood vessels, there is difficulty in passing through the blood-brain barrier. Therefore, in order to maximize the effect of treatment of Alzheimer's dementia using stem cells, it is most important to repeatedly administer the stem cells into an exact location in the brain of a patient.

However, until now there have been no internationally available devices capable of administering stem cells into the brain and no internationally available cases of treatment of Alzheimer's disease using these devices, and thus, there are many difficulties in a procedure of administering stem cells into the brain of a patient.

In addition, when a delivery device is used for administration of stem cells, the stem cells may not be administered into a correct location because a guide is bent even though a navigation system for brain surgery is used, and thus, there is a risk that accuracy of a procedure is reduced. This problem is similarly reproduced even in a case of repeated administration, and particularly, in the case of repeated administration into the same site, the guide is still inaccurate and the same procedure has to be performed again, and in this regard, it must be quite cumbersome for patients.

DESCRIPTION OF EMBODIMENTS

Technical Problem

The present disclosure is to solve many problems including the above-described problems, and an object of the present disclosure is to provide an apparatus for intracranial drug injection and a method for intracranial drug injection by which stem cells or brain disease treatment drugs may be easily and repeatedly administered into an affected brain lesion of a patient suffering from a degenerative brain disease such as Alzheimer's dementia. However, the problems are exemplary, and the scope of the present disclosure is not limited thereby.

Solution to Problem

Embodiments of the present disclosure are to provide an apparatus for intracranial drug injection and a method for intracranial drug injection.

According to an aspect of the present disclosure, there is an apparatus for intracranial drug injection including a body unit having a through-hole extending between a first opening in a topmost surface and a second opening in a bottommost surface, a cap unit having a shape corresponding to at least a part of an inner surface of the through-hole and being inserted into the first opening to cover the first opening, and a tube unit having one end coupled to the second opening and the other end extending toward an affected brain lesion.

Advantageous Effects of Disclosure

According to one embodiment of the present disclosure made as described above, an operation of repeatedly administering stem cells or brain disease treatment drugs to an affected brain lesion of a patient may be safely performed.

In addition, sufficiently administering the stem cells or the brain disease treatment drugs without incising the skin may be performed, and thus, a surgical procedure may be simplified, and a physical pain and economic burden of the patient may be reduced.

It is natural that the scope of the present disclosure is not limited by the effects.

BRIEF DESCRIPTION OF DRAWINGS

FIGS. 5 to 11 are cross-sectional views sequentially illustrating a method for intracranial drug injection according to an embodiment of the present disclosure.

BEST MODE

Figure 1:
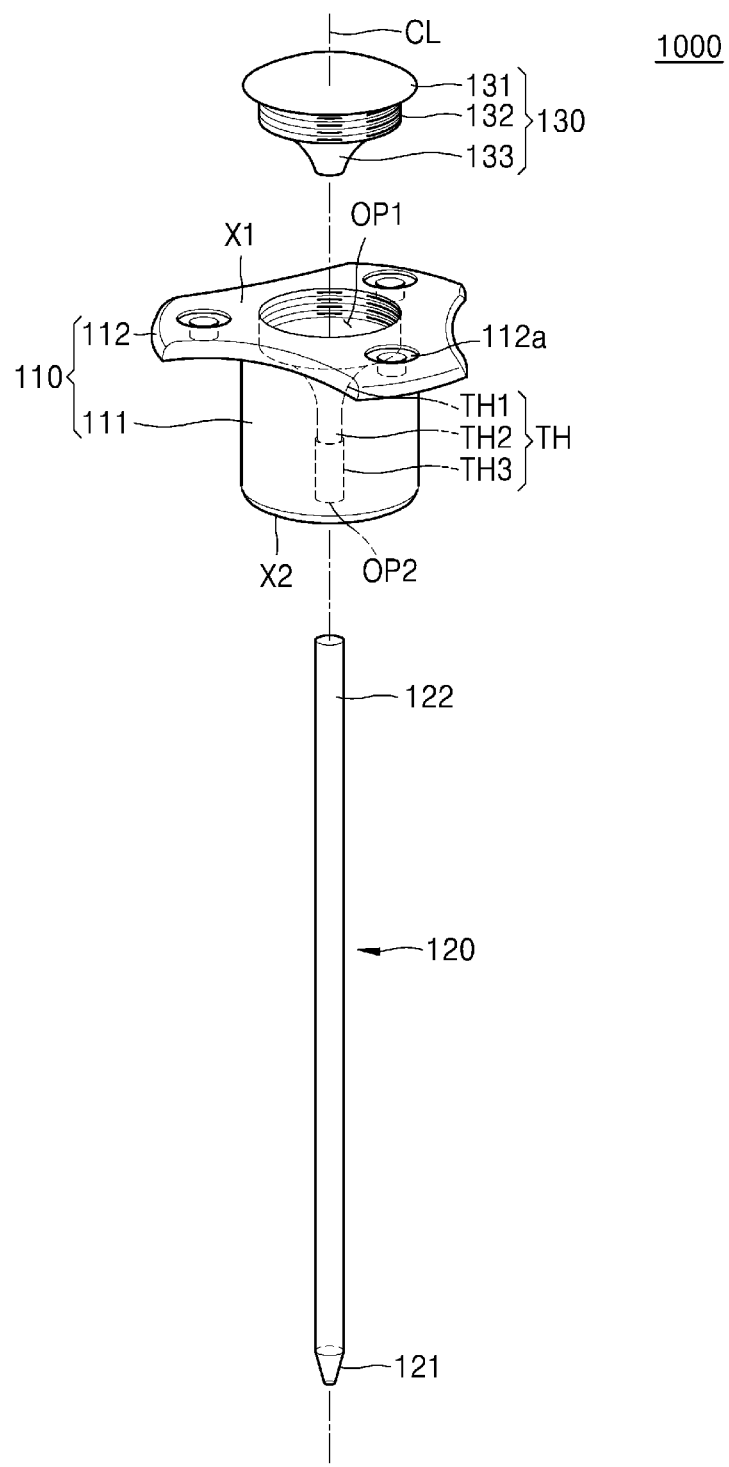
FIG. 1 is an exploded perspective view schematically illustrating an apparatus for intracranial drug injection according to an embodiment of the present disclosure.

According to an aspect of the present disclosure, there is an apparatus for intracranial drug injection including a body unit having a through-hole extending between a first opening in a topmost surface and a second opening in a bottommost surface, a cap unit having a shape corresponding to at least a part of an inner surface of the through-hole and being inserted into the first opening to cover the first opening, and a tube unit having one end coupled to the second opening and the other end extending toward an affected brain lesion.

The through-hole may include a first through unit into which the cap unit is inserted, a third through unit into which the tube unit is inserted, and a second through unit connecting the first through unit to the third through unit.

A cross-sectional area of the first through unit in a direction of the topmost surface may be larger than a cross-sectional area in a direction of the bottommost surface.

An inner surface of the first through unit may have a funnel shape.

A unit of the cap unit inserted into the first through unit may have a shape corresponding to the inner surface of the first through unit.

At least a part of the first through unit may be screwed with the cap unit.

A cross-sectional area of the second through unit may be smaller than a cross-sectional area of the third through unit.

The body unit may include a column unit having a through-hole formed therein, and a flange unit that extends from the column unit, protrudes to the outside of the column unit, and has a plurality of screw holes surrounding the first opening.

The cap unit may include a light-transmitting material.

The cap unit may include silicone.

The tube unit may be inserted into the second opening of the body unit.

The tube unit may be formed integrally with the body unit.

The cap unit may be formed integrally with the body unit.

According to another aspect of the present disclosure, there is a method for intracranial drug injection that includes (a) a step of preparing an apparatus for intracranial drug injection including a body unit having a through-hole extending between a first opening in a topmost surface and a second opening in a bottommost surface, a cap unit having a shape corresponding to at least a part of an inner surface of the through-hole, and a tube unit coupled to the second opening of the through hole, (b) a step of perforating a hole in a skull of a patient suffering from a degenerative brain disease including Alzheimer's dementia, (c) a step of inserting an assembly of the body unit, the cap unit, and the tube unit into brain parenchyma of the patient through the hole, (d) a step of inserting a guiding rod into the tube unit to guide an end of the tube unit to move in a direction of an affected brain lesion of the patient, (e) a step of removing the guiding rod from the combination after the body unit is coupled to a skull when the end of the tube unit reaches the affected brain lesion, and (f) a step of inserting a needle of a syringe storing drugs into the tube unit through the cap unit to supply the drugs to the affected brain lesion.

The method may further include (g) a step of passing the needle of the syringe storing the drugs through a unit of skin overlapping the cap unit and sutured to cover the skull and repeating step (f).

The body unit may include a column unit having a through-hole formed therein, and a flange unit that extends from the column unit, protrudes to the outside of the column unit, and has a plurality of screw holes surrounding the first opening.

Step (e) may include a step of interposing a support unit between the flange unit and a skull, and thereafter, inserting a screw into the plurality of screw holes to couple the flange unit to the skull.

The support unit may have a wedge shape.

The cap unit may include a light-transmitting material.

The cap unit may include silicone.

MODE OF DISCLOSURE

The present disclosure may be subjected to various modifications and have various embodiments, and specific embodiments will be illustrated in the drawings and described in detail in the detailed description. However, this is not intended to limit the present disclosure to specific embodiments, and should be understood to include all modifications, equivalents, and substitutes included in the idea and scope of the present disclosure. In the description of the present disclosure, when it is determined that a detailed description of known technologies related to the present disclosure may obscure the subject matter of the present disclosure, the detailed description will be omitted.

Terms such as first and second used in the present specification may be used to describe various configuration elements, but the configuration elements should not be limited by terms. The terms are used only to distinguish one configuration element from other configuration elements.

Hereinafter, embodiments according to the present disclosure will be described in detail with reference to the drawings, and in describing the embodiments with reference to the drawings, substantially the same or corresponding configuration elements are denoted by the same reference numerals, and redundant description thereof will be omitted. In the drawings, thicknesses are enlarged to clearly represent various layers and regions. In the drawings, thicknesses of some layers and regions are exaggerated for the sake of convenient description.

Figure 2:
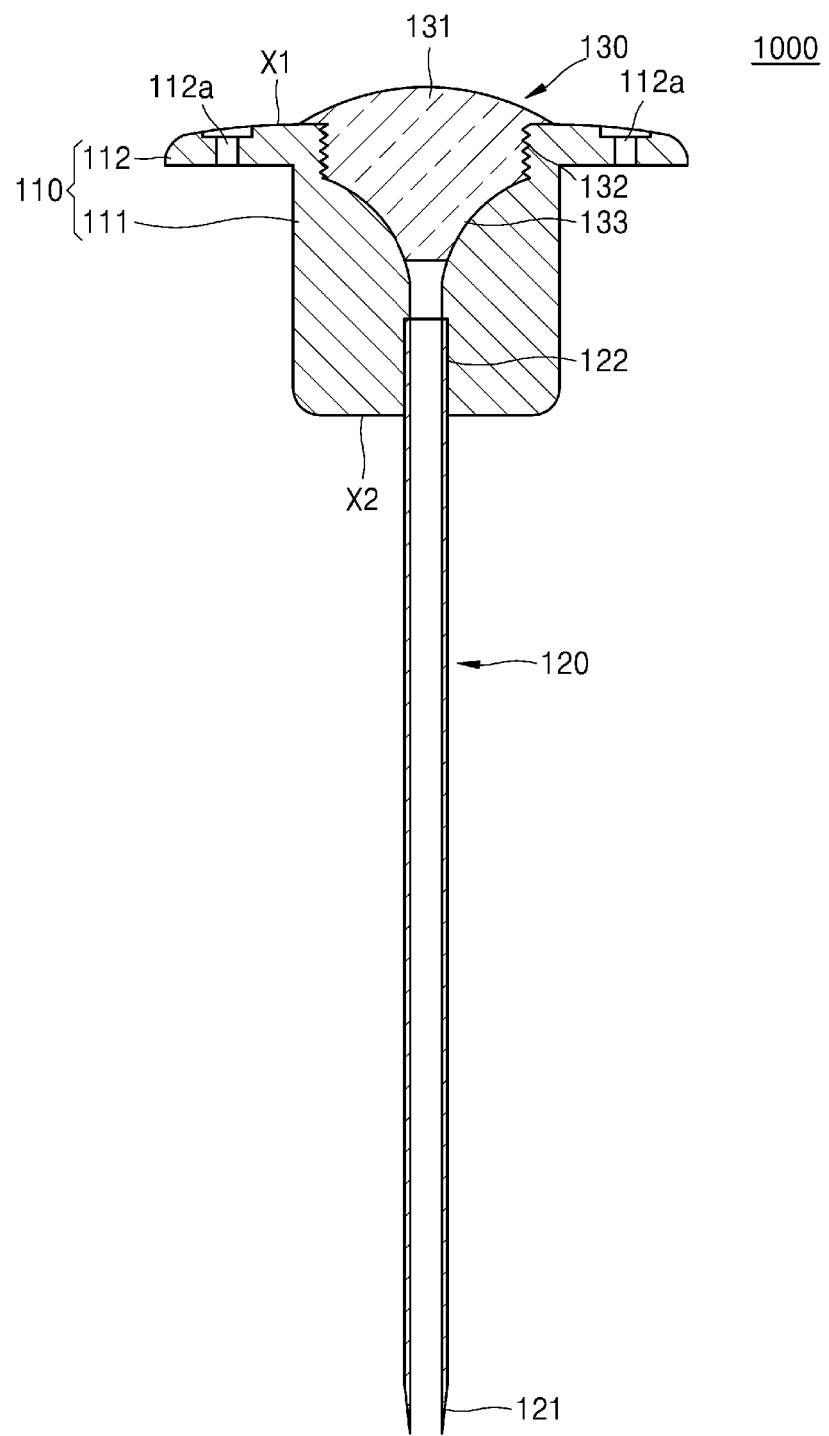
FIG. 2 is a cross-sectional view schematically illustrating the apparatus for intracranial drug injection of FIG. 1.
Figure 3:
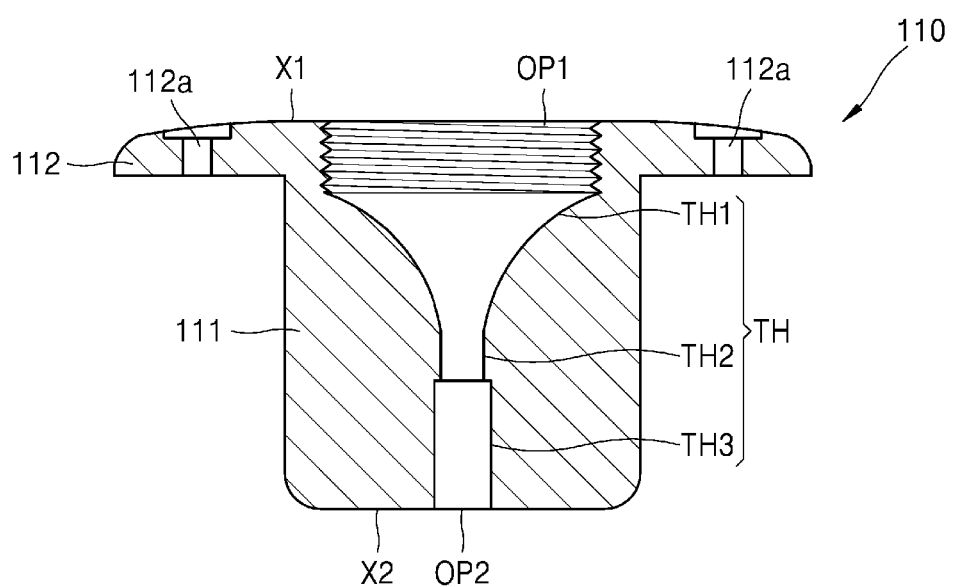
FIG. 3 is a cross-sectional view schematically illustrating a body unit of FIG. 1.

FIG. 1 is an exploded perspective view schematically illustrating an apparatus for intracranial drug injection according to an embodiment of the present disclosure, FIG. 2 is a cross-sectional view schematically illustrating the apparatus for intracranial drug injection of FIG. 1, and FIG. 3 is a cross-sectional view schematically illustrating a body unit of FIG. 1.

Referring to FIGS. 1 to 3, an apparatus 1000 for intracranial drug injection according to the embodiment of the present disclosure includes a body unit 110, a tube unit 120, and a cap unit 130.

First, the body unit 110 has a through-hole TH in the center, and specifically, the through-hole TH extends between a first opening OP1 formed on a topmost surface X1 of the body unit 110 and a second opening OP2 formed in a bottommost surface X2 of the body unit 110. By doing so, a drug injection tool, such as a syringe may enter or exit the apparatus 1000 for intracranial drug injection through the through-hole TH.

The through-hole TH includes a first through unit TH1, a second through unit TH2, and a third through unit TH3, as illustrated in FIG. 3.

The first through unit TH1 in the through-hole TH is a unit into which the cap unit 130 is inserted and may be divided into a unit to be screwed with the cap unit 130 and a unit coming into close contact with the cap unit 130 in a wide sense. Among these, the unit to be screwed with the cap unit 130 is located on an upper unit of the first through unit TH1 and may have a spiral groove formed to correspond to a thread of the cap unit 130 in an inner surface thereof so that the cap unit 130 may be screwed to the body unit 110. It is natural that the present disclosure is not limited thereto, and the spiral groove may be formed on an outer circumferential surface of the cap unit 130, and the thread may be formed in a unit to be screwed with the cap unit 130.

The unit coming into close contact with the cap unit 130 in the first through unit TH1 is located under the first through unit TH1 and has a shape corresponding to the cap unit 130 to come into close contact with the cap unit 130. The unit coming into close contact with the cap unit 130 may have a cross-sectional area in a topmost surface X1 direction larger than a cross-sectional area in a bottommost surface X2 direction and may be formed to have a funnel shape as an embodiment. However, the present disclosure is not limited thereto, and the unit coming into close contact with the cap unit 130 may be simply formed to have a tapered shape. As such, as the cross-sectional area of the first through unit TH1 in the direction of the topmost surface X1 is formed to be relatively large, a syringe and so on may be easily inserted into the first through unit TH1. In addition, the closer the first through unit TH1 is to the second through unit TH2, the more the cross-sectional area of the first through unit TH1 is reduced, and thus, only needle of a syringe passes therethrough, resulting in enabling a dose of administered drugs to be finely controlled.

The third through unit TH3 is a unit into which the tube unit 120 is inserted in the through-hole TH, and an inner diameter of the third through unit TH3 may be formed to be larger than an outer diameter of the tube unit 120. Although not illustrated in FIG. 1 and so on, the tube unit 120 and the third through unit TH3 may be screwed together.

The second through unit TH2 connects the first through unit TH1 to the third through unit TH3 and may have an inner diameter smaller than the inner diameter of the third through unit TH3 as illustrated in FIG. 3. For example, the inner diameter of the second through unit TH2 may be approximately the same as an inner diameter of the tube unit 120 to be inserted into the third through unit TH3. In addition, an inner surface of the second through unit TH2 may be formed to extend from the inner surface of the first through unit TH1. As a result, the tube unit 120 inserted into the first through unit TH1, the second through unit TH2, and the third through unit TH3 may function as an integral through-hole extending from the topmost surface X1 to the bottommost surface X2.

Meanwhile, the body unit 110 may be divided into a column unit 111 and a flange unit 112 depending on a shape of the outer circumferential surface. As illustrated in FIG. 1, the column unit 111 has a column shape, and most of the through-hole TH is formed inside the column unit 111. The column unit 111 does not necessarily need to be a column and may have various shapes such as a taper and a polygonal column.

The flange unit 112 extends from the column unit 111 and is located above the column unit 111. The flange unit 112 has a plate shape and is formed to protrude outside the column unit 111. A first opening OP1 is formed on the topmost surface X1 of the flange unit 112, where the first opening OP1 corresponds to an inlet of the first through unit TH1 into which the cap unit 130 is inserted. Therefore, a unit, which is screwed with the cap unit 130, in the first through units TH1 may be located in the flange unit 112.

In addition, the flange unit 112 includes a plurality of screw holes 112a surrounding the first opening OP1. Although three screw holes 112a are illustrated in FIG. 1, the present disclosure is not limited thereto, and two or more screw holes 112a may be formed. As a result, fastening members such as screws, bolts, or pins may be inserted into the plurality of screw holes 112a to firmly couple the flange unit 112 to the skull of a patient.

Next, the tube unit 120 is an elongated thin member having a tubular shape, and a second end 122 of the tube unit 120 may be inserted into the second opening OP2 of the body unit 110. A first end 121 of the tube unit 120 approaches an affected brain lesion of a patient and may be sharply processed into a tapered shape to be easily inserted into a brain tissue. A needle of a syringe or so on is inserted into the tube unit 120 to supply drugs discharged from the needle of the syringe to the affected unit located near the first end 121. Therefore, a length of the tube unit 120 may be variously adjusted depending on a location of the affected brain lesion.

Meanwhile, although FIG. 1 and so on illustrate the tube unit 120 and the body unit 110 as separate members, the present disclosure is not limited thereto. That is, the tube unit 120 and the body unit 110 may be integrally formed.

Next, the cap unit 130 is a member that is inserted into the first opening OP1 of the body unit 110 to cover the first opening OP1. The cap unit 130 may be divided into three units: a cover unit 131, a thread unit 132, and a close contact unit 133.

Among the units, the cover unit 131 may cover the first opening OP1 and may be formed to be larger than a size of the first opening OP1 to block the first opening OP1 from the outside. As a result, foreign materials are prevented from flowing in a brain tissue through the first opening OP1 from the outside. The cover unit 131 has a thin plate shape and may be processed into a hilly shape of which a central unit is raised.

The thread unit 132 extending from the cover unit 131 is formed to have a thread on an outer surface thereof. Accordingly, the thread unit 132 of the cap unit 130 may be coupled to a spiral groove formed at the center of the flange unit 112. That is, the thread unit 132 is coupled to a unit, which is screwed with the cap unit 130, in the first through unit TH1.

The close contact unit 133 extending from the thread unit 132 has a cross-sectional area that is gradually reduced. The close contact unit 133 has a shape corresponding to an inner surface of the unit, which comes into close contact with the cap unit 130, in the first through unit TH1, whereby close the contact unit 133 may be fitted to the unit, which comes into close contact with cap unit 130, in the first through unit TH1.

In addition, the cap unit 130 may be formed of a flexible material so that a needle of a syringe or so on may pass therethrough. In addition, the cap unit 130 may be formed of a transparent or translucent material so that the needle of the syringe or so on may be accurately inserted into the second through unit TH2 and the third through unit TH3 having relatively small inner diameters. That is, the cap unit 130 may include a light-transmitting material. In one embodiment, the cap unit 130 may be formed of flexible and light-transmitting silicone.

The body unit 110, the tube unit 120, and the cap unit 130 described above are members to be installed inside the body of a patient, and thus, being required to be formed of a material of medical grade. In addition, the body unit 110, the tube unit 120, and the cap unit 130 are preferably formed of a non-metallic material to enable MRI imaging and so on.

Figure 4:
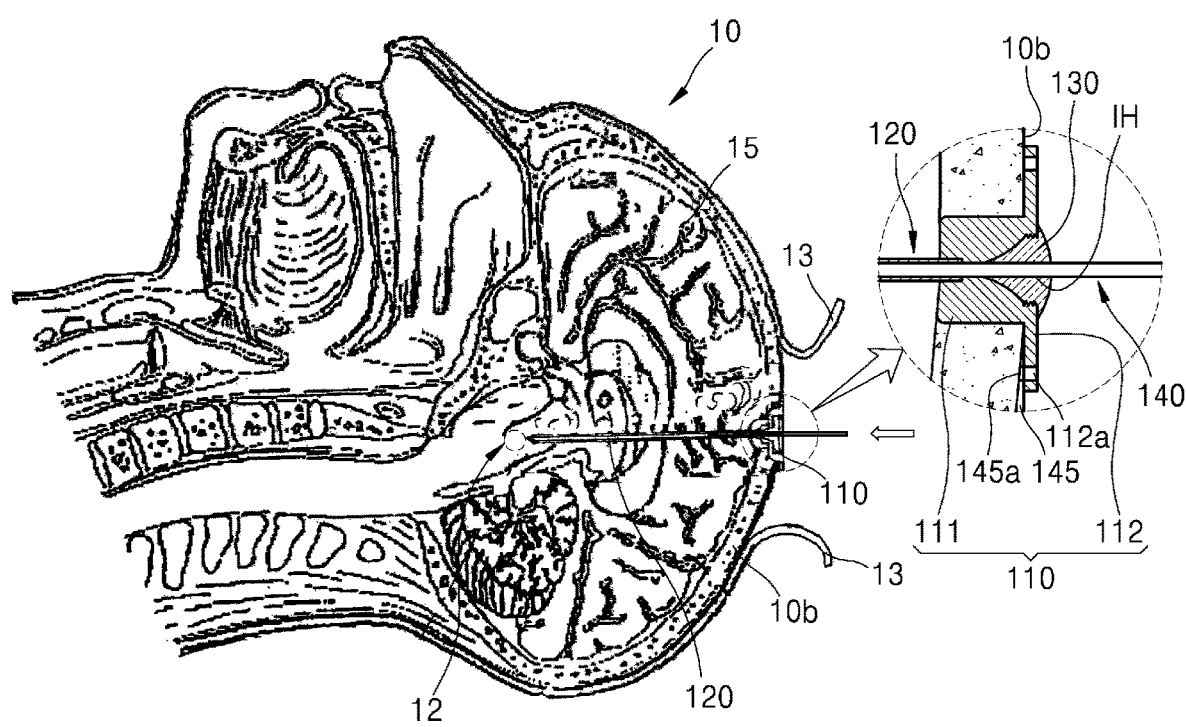
FIG. 4 is a cross-sectional view illustrating a state in which a unit of the apparatus for intracranial drug injection according to the embodiment of the present disclosure is installed on the head of a patient.

FIG. 4 is a cross-sectional view illustrating a state in which a unit of the apparatus for intracranial drug injection according to the embodiment of the present disclosure is installed on the head of a patient.

As illustrated in FIG. 4, the apparatus 1000 for intracranial drug injection is installed on a head 10 of an Alzheimer's dementia patient. at this time, the apparatus 1000 for intracranial drug injection to be installed on the head 10 of the patient means that the body unit 110, the tube unit 120, and the cap unit 130 are coupled to each other.

The body unit 110 is coupled to a skull 10b of the patient, and because the skull 10b of the patient has a curved surface, when the flange unit 112 is coupled onto the skull 10b of the patient, a phenomenon in which the flange unit is lifted or crooked may occur. In order to solve this problem, a support unit 145 may be interposed between the flange unit 112 and the skull 10b. Accordingly, a screw may be stably inserted into the skull 10b by flattening a lower unit of the flange unit 112.

The support unit 145 may have a wedge shape to fill an inclined gap between the flange unit 112 and the skull 10b. However, when the inclination of the gap is not severe, the support unit 145 may be formed in a plate shape having a constant thickness. In addition, a separate screw hole 145a may be formed in the support unit 145 so that the screw is inserted into the skull 10b under the support unit 145. At this time, it is necessary to properly adjust a location of the support unit 145 so that a screw hole 145a of the support unit 145 may be connected to the screw hole 112a of the flange unit 112.

Meanwhile, a guiding rod 140 is inserted into the tube unit 120 so that the tube unit 120 may reach the affected brain lesion of a patient through the shortest distance. The guiding rod 140 is a straight rod and guides the tube unit 120 in a direction of the affected brain lesion. Therefore, the guiding rod 140 may be formed to have a thickness that may be fitted inside the tube unit 120 and may be formed of a material having a high strength so as not to be bent when being inserted into the brain tissue. For example, the guiding rod 140 may be formed to include at least one of titanium, nitinol, and stainless steel.

In addition, the guiding rod 140 may be processed to have a shape corresponding to an inner surface of the tube unit 120 to maintain a shape of the tube unit 120 during a guiding process. Therefore, an end of the guiding rod 140 in the direction of the affected unit may also be sharply formed to correspond to a shape of an end of the tube unit 120 approaching the affected unit.

Hereinafter, a process of administering drugs into the affected brain lesion by installing an apparatus for intracranial drug injection in the skull of a patient will be described in detail with reference to FIGS. 5 to 11.

FIGS. 5 to 11 are cross-sectional views sequentially illustrating a method for intracranial drug injection according to an embodiment of the present disclosure.

Figure 5:
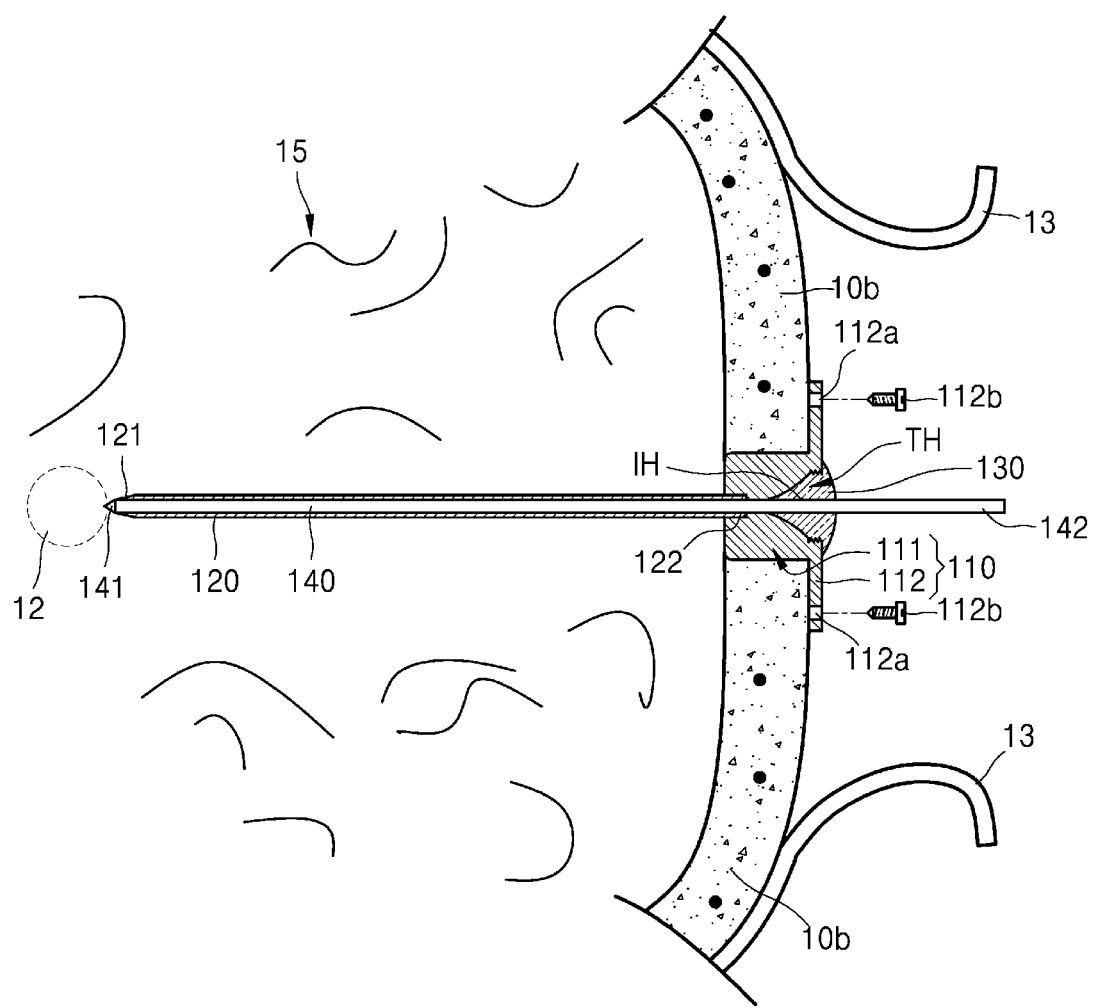

First, as illustrated in FIG. 5, the apparatus 1000 for intracranial drug injection illustrated in FIG. 1 and so on is prepared, and the skull 10b of the head of a patient suffering from Alzheimer's dementia is perforated. At this time, it is natural that a skin 13 covering the skull 10b is incised to expose a perforated location of the skull 10b.

Subsequently, the apparatus 1000 for intracranial drug injection which is a combination of the tube unit 120, the body unit 110, and the cap unit 130 is installed inside a hole formed in the skull 10b, and the guiding rod 140 passes through a raised unit of the center of the cap unit 130 in a state where the cap unit 130 is coupled to the body unit 110. Accordingly, an insertion hole IH extending from the cap unit 130 to the tube unit 120 is formed, and the guiding rod 140 is inserted into the tube unit 120 through the insertion hole IH to guide the first end 121 of the tube unit 120 to move in a direction of the affected unit 12 in brain parenchyma 15 of the patient. When the first end 121 of the tube unit 120 reaches the affected unit 12 through the guiding process, the body unit 110 is coupled to the skull 10b. Specifically, screws 112b are inserted into a plurality of screw holes 112a formed in the flange unit 112 to fasten the flange unit 112 to the skull 10b.

At this time, as illustrated in FIG. 4, a support unit may be interposed between the flange unit 112 and the skull 10b depending on the perforated location of the skull (10b). However, hereinafter, for the sake of convenient description, a description will be made specifically for a case where the support unit is omitted.

Figure 6:
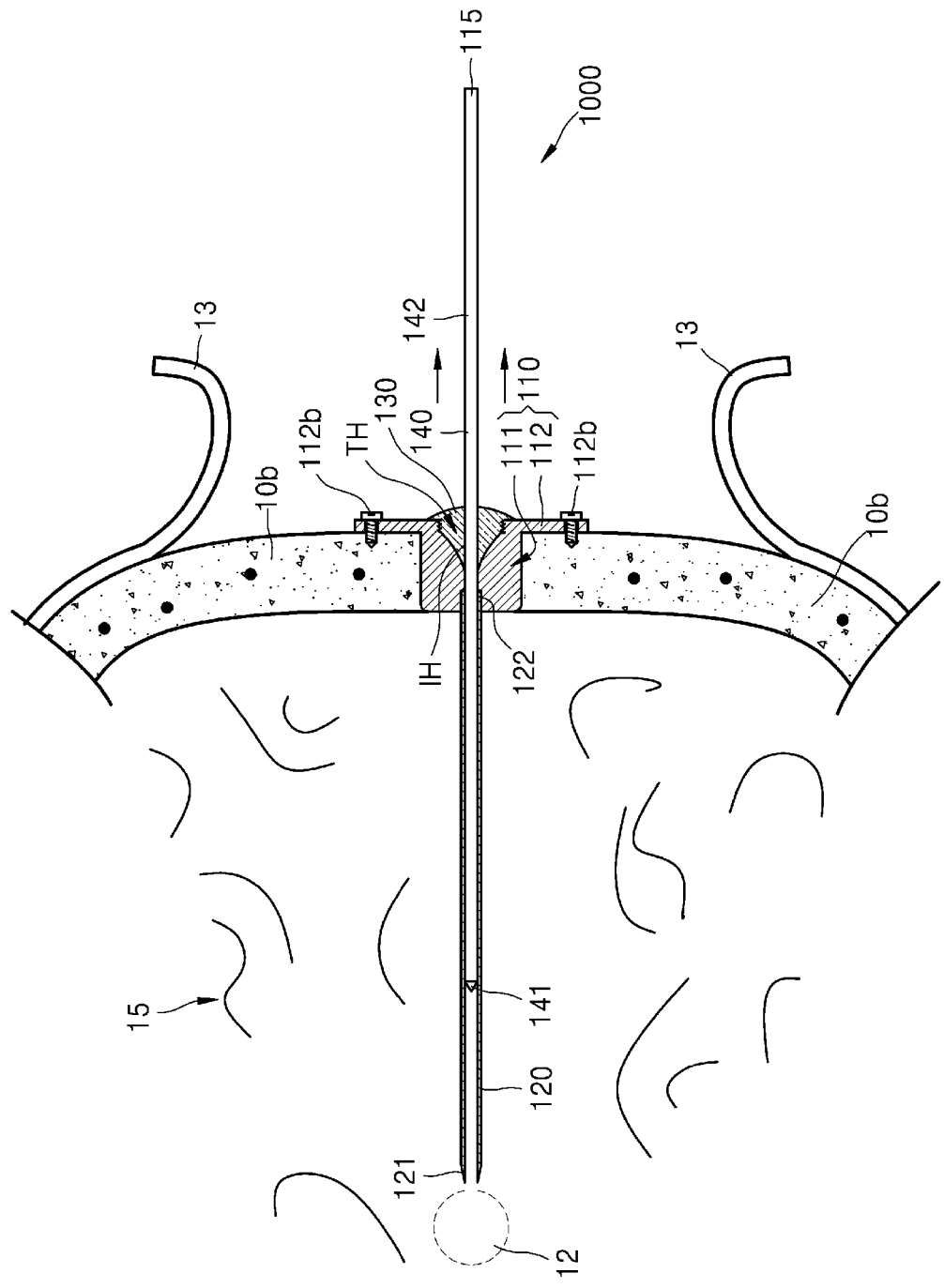
Figure 7:
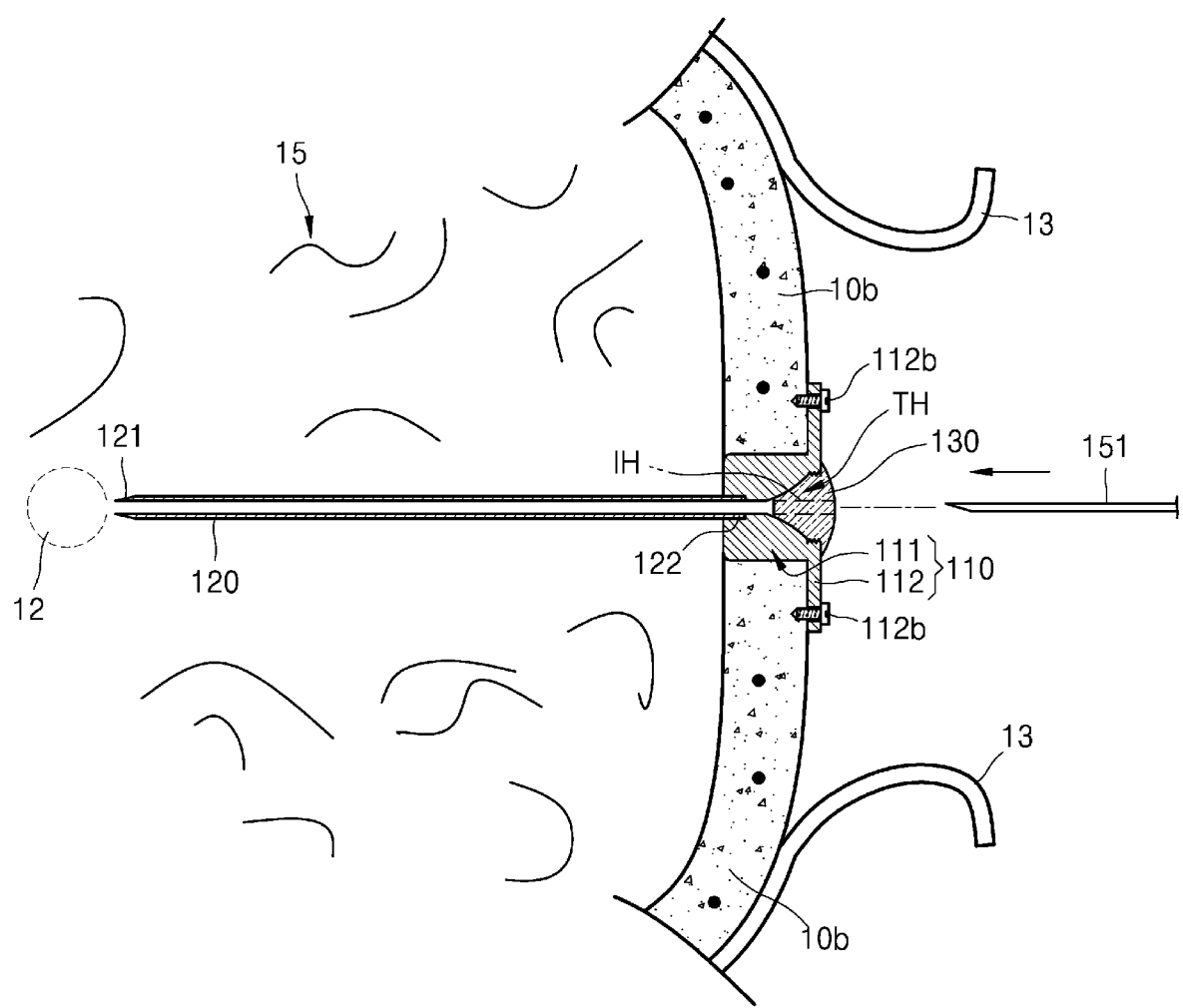

Next, the guiding rod 140 is removed from the apparatus 1000 for intracranial drug injection as illustrated in FIG. 6, and then, a needle 151 of a syringe is inserted from the cap 130 into the tube unit 120 through the insertion hole IH extending to the tube unit 120 as illustrated in FIG. 7. At this time, the needle 151 of the syringe moves to the first end 121 of the tube unit 120 located near the affected unit.

Figure 8:
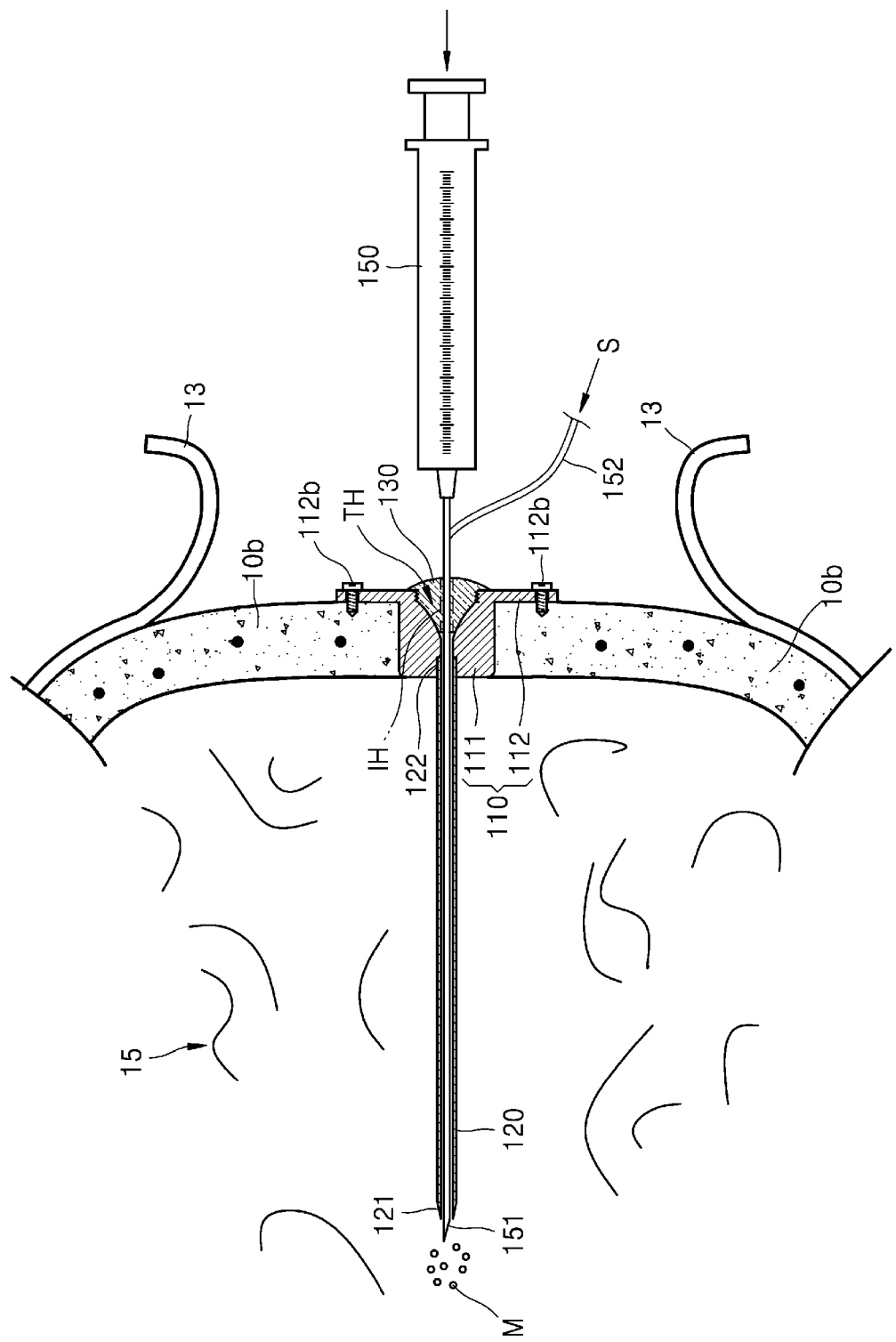

Next, as illustrated in FIG. 8, the syringe 150 is operated to supply drugs M stored in the syringe to the affected brain lesion. Here, the drugs M are to treat a degenerative brain disease including the Alzheimer's dementia and may be, for example, stem cells.

As such, the drugs M are administered by a predetermined amount, and thereafter, the needle 151 of the syringe is removed from the apparatus 1000 for intracranial drug injection. At this time, while pulling out the needle 151 of the syringe, saline solution S may be injected through a saline solution supply pipe 152. Meanwhile, although not illustrated in FIG. 8, at least a part of an inner passage of the insertion hole (IH) remaining in the cap unit 130 after removing the needle 151 of the syringe may be filled due to material characteristics (for example, silicone) of the cap unit 130, and thus, an inflow of foreign materials from the outside may be minimized.

Figure 9:
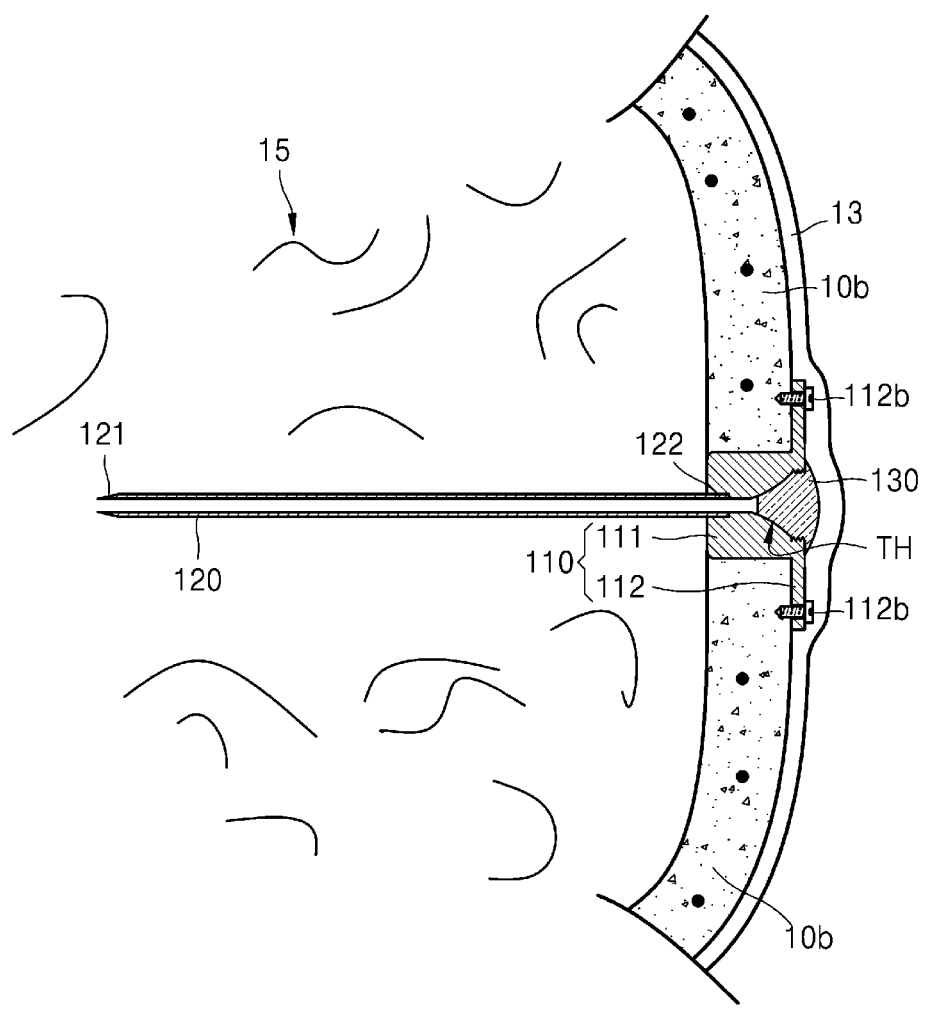

Next, as illustrated in FIG. 9, the skin 13 is sealed to completely cover the apparatus 1000 for intracranial drug injection. By doing so, a process of administering drugs into the brain of a patient suffering from Alzheimer's dementia once is completed.

Meanwhile, if three to six months elapse after the drugs M such as stem cells are administered for the first time, an effect of the drugs M is reduced, and thus, it is necessary to repeatedly administer the drugs M at the elapsed time point. That is, when the drugs are repeatedly administered into the brain of a patient after a predetermined period elapses, the following process is performed.

Figure 10:
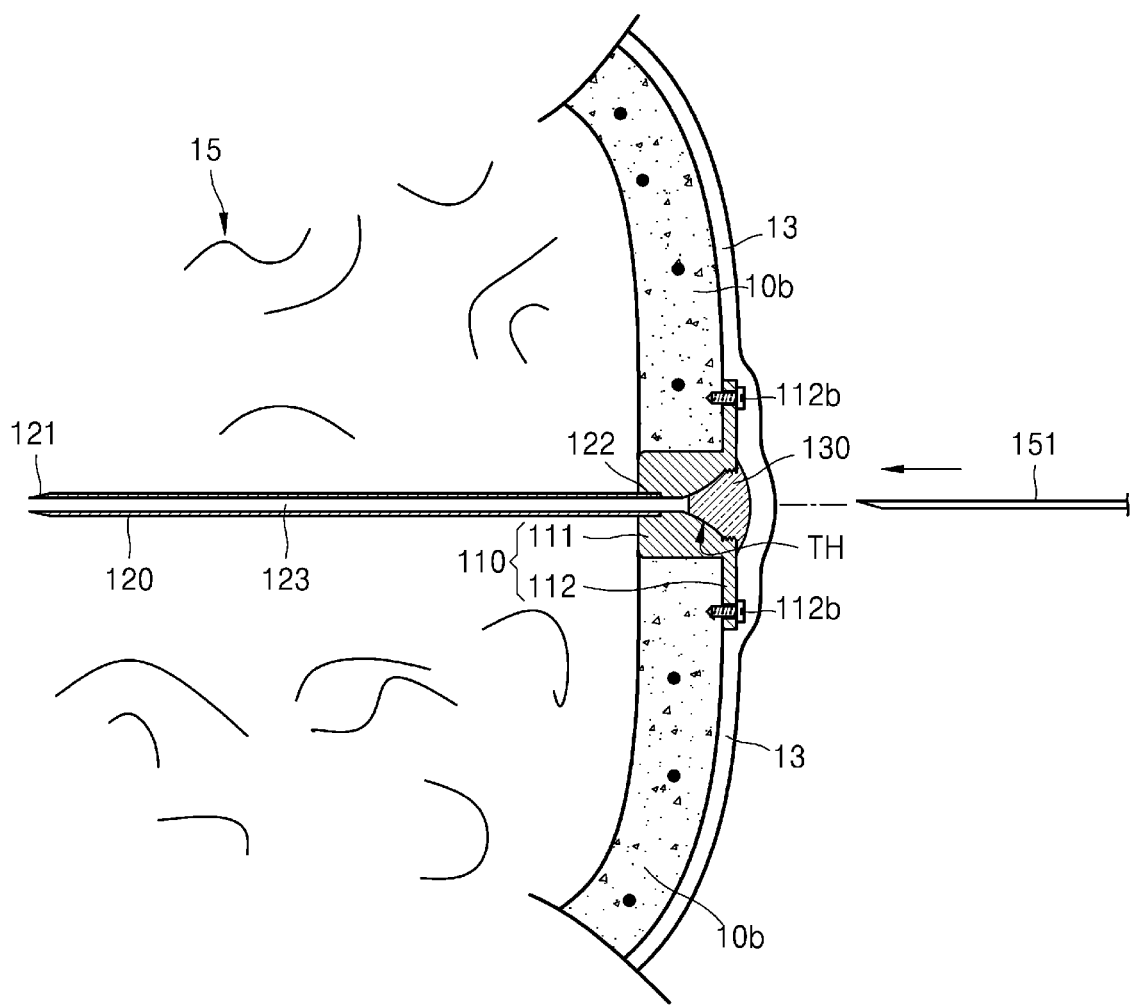

First, as illustrated in FIG. 10, the needle 151 of the syringe is inserted into the apparatus 1000 for intracranial drug injection installed in the brain of the patient. Specifically, in a state in which the cap unit 130 is buried under the skin 13, the needle 151 of the syringe passes through a unit of the skin 13 overlapping the center of the cap unit 130. At this time, the unit of the skin 13 through which the needle 151 of the syringe passes may protrude to the outside to correspond to the raised shape of the center of the cap unit 130.

As such, the cap unit 130 may be formed of a flexible material so that the needle 151 of the syringe is properly inserted into the tube unit 120 through the cap unit 130. In addition, the cap unit 130 may be formed of a light-transmitting material. For example, the cap unit 130 may include silicone.

Next, as illustrated in FIG. 11, the needle 151 of the syringe is inserted into the tube unit 120 to reach the affected brain lesion of the patient. Thereafter, a process of supplying the therapeutic drugs M stored in the syringe 150 to the affected brain lesion of the patient by operating the syringe 150 is repeated.

According to the method for intracranial drug injection illustrated in FIGS. 10 and 11, when the drugs need to be repeatedly administered into the brain of a patient, only the needle 151 of the syringe has to be inserted into the apparatus 100 for intracranial drug injection previously installed without a need for a complicated injection process. At this time, since the needle 151 of the syringe may pass through the cap unit 130 without dividing the cap unit 130, much of a cumbersome process of perforating the head of a patient and inserting the syringe 150 thereinto may be omitted. In addition, since the drugs M are administered in a state in which the cap unit 130 covers the through-hole TH of the body unit 110, an inflow of foreign materials and so on into the brain may be minimized.

As described above, when using an apparatus for intracranial drug injection and/or a method for intracranial drug injection according to an embodiment of the present disclosure, an operation of repeatedly administering stem cells or brain disease treatment drugs to an affected brain lesion of a patient may be safely performed. In addition, sufficiently administering the stem cells or the brain disease treatment drugs without incising the skin may be performed, and thus, a surgical procedure may be simplified, and a physical pain and economic burden of the patient may be reduced.

As described above, the present disclosure is described with reference to one embodiment illustrated in the drawings, this is only an example, and those skilled in the art will understand that various modifications and modifications of the embodiment may be made therefrom. Therefore, the true technical protection scope of the present disclosure should be determined by the technical idea of the appended claims.

INDUSTRIAL APPLICABILITY

According to an embodiment of the present disclosure, there is an apparatus for intracranial drug injection and a method for intracranial drug injection that may administer repeatedly and safely stem cells or brain disease treatment drugs into an affected brain lesion of a patient, the apparatus for intracranial drug injection and the method for intracranial drug injection may be used for treatment of a patient suffering from a degenerative brain disease such as Alzheimer's dementia or a patient who underwent brain surgery and may also be used for treatment of various patients requiring drug injection into the brain.

The invention claimed is:

1. An apparatus for intracranial drug injection comprising:
a body unit having a through-hole extending between a first opening in a topmost surface and a second opening in a bottommost surface;
a cap unit having a shape corresponding to at least a part of an inner surface of the through-hole and being inserted into the first opening to cover the first opening; and
a tube unit having one end coupled to the second opening and the other end configured to extend toward a brain lesion,
wherein the through-hole comprises:
a first through unit into which the cap unit is inserted;
a third through unit into which the tube unit is inserted; and
a second through unit connecting the first through unit to the third through unit, and wherein a cross-sectional area of the second through unit is smaller than a cross-sectional area of the third through unit, and
wherein the first through unit, the second through unit, and the third through unit extend continuously inside the body unit which is formed as one piece.

2. The apparatus for intracranial drug injection of claim 1, wherein a cross-sectional area of a topmost surface of the first through unit is larger than a cross-sectional area of a bottommost surface of the first through unit.

3. The apparatus for intracranial drug injection of claim 2, wherein an inner surface of the first through unit has a funnel shape.

4. The apparatus for intracranial drug injection of claim 3, wherein a unit of the cap unit inserted into the first through unit has a shape corresponding to the inner surface of the first through unit.

5. The apparatus for intracranial drug injection of claim 1, wherein at least a part of the first through unit is screwed with the cap unit.

6. The apparatus for intracranial drug injection of claim 1, wherein the body unit comprises:
a column unit having the through-hole formed therein; and
a flange unit that extends from the column unit, protrudes to the outside of the column unit, and has a plurality of screw holes surrounding the first opening.

7. The apparatus for intracranial drug injection of claim 1, wherein the cap unit includes a light-transmitting material.

8. The apparatus for intracranial drug injection of claim 6, wherein the cap unit includes silicone.

9. The apparatus for intracranial drug injection of claim 6, wherein the tube unit is inserted into the second opening of the body unit.

10. The apparatus for intracranial drug injection of claim 1, wherein the tube unit is formed integrally with the body unit.

11. The apparatus for intracranial drug injection of claim 1, wherein the cap unit is formed integrally with the body unit.

12. A method for intracranial drug injection comprising:
(a) a step of preparing an apparatus for intracranial drug injection including a body unit having a through-hole extending between a first opening in a topmost surface and a second opening in a bottommost surface, a cap unit having a shape corresponding to at least a part of an inner surface of the through-hole, and a tube unit coupled to the second opening of the through hole;
(b) a step of perforating a hole in a skull of a patient suffering from a degenerative brain disease including Alzheimer's dementia;
(c) a step of inserting a combination of the body unit, the cap unit, and the tube unit into brain parenchyma of the patient through the hole;
(d) a step of inserting a guiding rod into the tube unit to guide an end of the tube unit to move in a direction of a brain lesion of the patient;
(e) a step of removing the guiding rod from the combination after the body unit is coupled to the skull when the end of the tube unit reaches the brain lesion; and
(f) a step of inserting a needle of a syringe storing drugs into the tube unit through the cap unit to supply the drugs to the brain lesion, and
wherein the through-hole comprises:
a first through unit into which the cap unit is inserted;
a third through unit into which the tube unit is inserted; and a second through unit connecting the first through unit to the third through unit, and wherein a cross-sectional area of the second through unit is smaller than a cross-sectional area of the third through unit, and wherein the first through unit, the second through unit, and the third through unit extend continuously inside the body unit which is formed as one piece.

13. The method for intracranial drug injection of claim 12, further comprising:

(g) a step of passing the needle of the syringe storing the drug through a unit of skin of the patient overlapping the cap unit and sutured to cover the skull after step (f) and repeating step (f).

14. The method for intracranial drug injection of claim 12, wherein the body unit comprises:

a column unit having the through-hole formed therein; and a flange unit that extends from the column unit, protrudes to the outside of the column unit, and has a plurality of screw holes surrounding the first opening.

15. The method for intracranial drug injection of claim 14, wherein step (e) includes a step of interposing a support unit between the flange unit and the skull, and thereafter, inserting screws into the plurality of screw holes to couple the flange unit to the skull.

16. The method for intracranial drug injection of claim 15, wherein the support unit has a wedge shape.

17. The method for intracranial drug injection of claim 12, wherein the cap unit includes a light-transmitting material.

18. The method for intracranial drug injection of claim 12, wherein the cap unit includes silicone.

\* \* \* \* \*